(12) United States Patent
Fafara

(10) Patent No.: US 10,152,572 B2
(45) Date of Patent: Dec. 11, 2018

(54) SOCIAL MEDIA DISSEMINATION OF HEALTH INFORMATION VIA A HYBRID ARCHITECTURE

(71) Applicant: Systems Made Simple, Inc., Tysons Corner, VA (US)

(72) Inventor: Glen Michael Fafara, Clearwater, FL (US)

(73) Assignee: SYSTEMS MADE SIMPLE, INC., Tysons Corner, VA (US)

( * ) Notice: Subject to any disclaimer, the term of this patent is extended or adjusted under 35 U.S.C. 154(b) by 625 days.

(21) Appl. No.: 14/613,199

(22) Filed: Feb. 3, 2015

(65) Prior Publication Data

US 2016/0225114 A1    Aug. 4, 2016

(51) Int. Cl.
| | | |
|---|---|---|
| *G16H 10/60* | (2018.01) | |
| *G06F 19/00* | (2018.01) | |
| *G06Q 10/10* | (2012.01) | |
| *G06Q 50/00* | (2012.01) | |
| *G06Q 50/24* | (2012.01) | |

(52) U.S. Cl.
CPC ........ *G06F 19/322* (2013.01); *G06F 19/3456* (2013.01); *G06Q 10/109* (2013.01); *G06Q 50/01* (2013.01); *G06Q 50/24* (2013.01); *G16H 10/60* (2018.01)

(58) Field of Classification Search
CPC ..... G06Q 50/22; G06Q 50/24; G06F 19/3456
See application file for complete search history.

(56) References Cited

U.S. PATENT DOCUMENTS

| | | | |
|---|---|---|---|
| 6,757,898 B1 * | 6/2004 | Ilsen | G06F 19/324 600/300 |
| 8,433,587 B1 | 4/2013 | Cullen | 705/3 |
| 2006/0129444 A1 | 6/2006 | Baeza et al. | |
| 2006/0229910 A1 | 10/2006 | Longman et al. | |
| 2008/0238666 A1 | 10/2008 | Loncar | |
| 2010/0299155 A1 | 11/2010 | Findlay et al. | |

(Continued)

OTHER PUBLICATIONS

Final Office Action dated Nov. 13, 2015 in corresponding U.S. Appl. No. 14/686,430 (14 pages).

*Primary Examiner* — Joseph D Burgess
(74) *Attorney, Agent, or Firm* — Pillsbury Winthrop Shaw Pittman LLP

(57) ABSTRACT

A system and method for communicating health care information and/or facilitating health care services via a hybrid architecture. The system may obtain and anonymize health care event information associated with an individual. The system may determine an authorized recipient of the anonymized health care information and generate a communication to the authorized recipient via a social media platform. The system may provide access to a non-anonymized version of the health care information to the authorized recipient. The system may receive and process a social media communication indicating a health care service. The system may generate a user request for the health care service based on information associated with the health care service. The system may provide the user request for the health care service to a health care service provider such that the health care service provider may fulfill, initiate, complete, and/or otherwise act upon the request.

18 Claims, 6 Drawing Sheets

(56) References Cited

U.S. PATENT DOCUMENTS

| | | | |
|---|---|---|---|
| 2010/0318379 A1* | 12/2010 | Demopulos | G06Q 10/10 |
| | | | 705/3 |
| 2011/0082705 A1 | 4/2011 | Kobylevsky et al. | 705/2 |
| 2012/0089518 A1* | 4/2012 | Blonchek | G06Q 10/10 |
| | | | 705/50 |
| 2012/0278101 A1 | 11/2012 | Homchowdhury et al. | 705/3 |
| 2013/0086163 A1 | 4/2013 | Neff | 709/204 |
| 2014/0088991 A1 | 3/2014 | Bakes et al. | 705/2 |
| 2014/0180708 A1 | 6/2014 | Advani | |
| 2014/0330842 A1 | 11/2014 | Knobel et al. | |
| 2015/0149208 A1 | 5/2015 | Lynch et al. | |
| 2015/0213203 A1* | 7/2015 | Cumbie | G06F 19/323 |
| | | | 705/3 |

* cited by examiner

SOCIAL MEDIA DISSEMINATION OF HEALTH INFORMATION VIA A HYBRID ARCHITECTURE

FIELD

The disclosure relates to a system and method for communicating health care information and/or facilitating health care services via a hybrid architecture.

BACKGROUND

In recent years, social media has become an increasingly important tool for businesses as the number of active social media users and the amount of time each user spends on social media continue to grow. Social media, for example, allows businesses to have direct communication with potential customers, and is a convenient way for potential customers to see such communications. Due to the private nature of health care information, and the legal risks involved with sharing such information, health care information related to individuals is generally not shared via social media. As such, the use of social media in the health care industry is typically restricted to providing general information or marketing materials to a non-specific group of people. These and other drawbacks exist.

SUMMARY

One aspect of the disclosure relates to a method and system for communicating health care information and/or facilitating health care services via a hybrid architecture (e.g., a social media component and a website), in accordance with one or more implementations. In an implementation, a system may obtain and anonymize health care information associated with one or more individuals to generate anonymized versions of the health care information (or the anonymized health care information) for the individuals, respectively. With regard to the anonymized health care information associated with a given individual, the system may identify one or more users of a social media platform as authorized receipts, and provide the anonymized health care information for presentation to the users via the social media platform. As an example, a social media communication may be generated via one or more social media addresses associated with the users (e.g., generating a post via a user's social media page address, via the user's account identifier on the social media platform, etc.).

The anonymized health care information may, for example, be provided with a link (e.g., URL) to a specific portion of a website (e.g., separate from the social media platform) that pertains to the health care information associated with the given individual. Responsive to providing the anonymized health care information and the link to the pertinent portion of the website, a request from an authorized receipt for access to the health care information may be received at the website. Upon determination that the request should be authorized, the system may provide access to a non-anonymized version of the health care information (e.g., via the website). In this way, health care information may be more conveniently accessed by authorized recipients (e.g., via the anonymized version, the non-anonymized version, etc.) while minimizing risk of regulatory violations (e.g., Health Insurance Portability and Accountability Act (HIPPA) violations) associated with the sharing of such information.

In an implementation, the system may enable users to request health care services (e.g., requests for more information regarding an event pertaining to an individual, requests for scheduling an appointment with a health care provider, requests for filling and/or refilling a prescription, etc.) via social media. In some implementations, the system may receive a social media communication of a user from a social media platform. The social media communication may, for example, indicate a health care service (e.g., requested by the user on behalf of the user, on behalf of an individual related to the user, etc.). The system may process the social media communication to determine the health care service and generate a user request for the health care service (e.g., based on information regarding a health care service provider that is able to provide the health care service, patient information of the individual (or the user) on whose behalf the health care service is requested, or other information). The user request may then be provided to the health care service provider. Among other benefits, the system facilitates health care services by enabling users to request and obtain health care services via a social media platform with which they are already familiar as active users, thereby reducing barriers to obtaining health care services.

In an implementation, the system may enable users to respond to its generated social media communications that include anonymized health care information. In some implementations, where a social media communication includes a link that enables a user to initiate one or more actions (e.g., requesting more information regarding an event pertaining to an individual, requesting scheduling of an appointment with a health care provider, requesting for filling and/or refilling of a prescription, etc.), the user may initiate the actions via the link. In some implementations, a user may respond to the system's social media communications by submitting a social media communication related to the anonymized information of the system's social media communications. The user's social media communication may, for example, be interpreted by the system to include a request for a particular health care service.

In some implementations, individuals whose health care information is shared, on whose behalf health care services are requested, etc., as described herein may include patients, subjects of a clinical trial, long-term care recipients, nursing home residents, residents of a psychiatric facility, rehabilitation participants, and/or other individuals. Social media platforms via which health care information is shared (e.g., anonymized versions) and/or via which health care services are requested may include Facebook, Twitter, Instagram, MySpace, Pinterest, Linked In, and/or other social media platforms.

These and other objects, features, and characteristics of the system and/or method disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular forms of "a", "an", and "the" include plural referents unless the context clearly dictates otherwise. In addition, as used in the specification and the claims, the term "or" means "and/or" unless the context clearly dictates otherwise.

DETAILED DESCRIPTION

Figure 1:
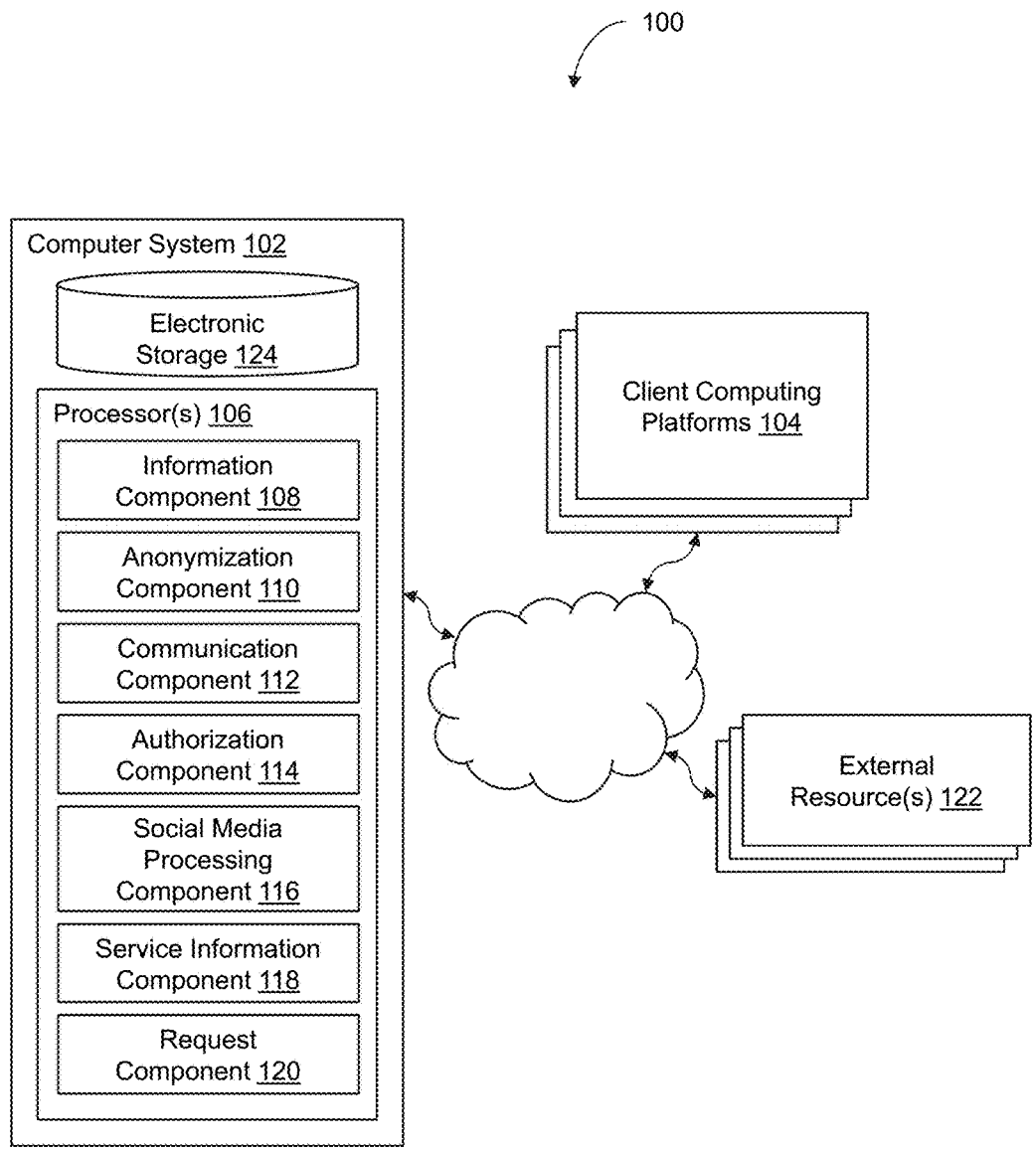
FIG. 1 illustrates a system for communicating health care information and/or facilitating health care services via a hybrid architecture, in accordance with an implementation.

FIG. 1 illustrates a system 100 for communicating health care information and/or facilitating health care services via a hybrid architecture, in accordance with an implementation. In some implementations, system 100 may include computer system 102 (e.g., one or more servers). Computer system 102 may be configured to communicate with one or more client computing platforms 104 in accordance with a client/server architecture. The users may access the system via client computing platforms 104.

Computer system 102 may include one or more processors 106. The one or more processors 106 may be programmed to execute one or more computer program components. The computer program components may comprise one or more of information component 108, anonymization component 110, communication component 112, authorization component 114, social media processing component 116, service information component 118, request component 120, and/or other components.

Communication of Information and/or Facilitation of Related Services

In an implementation, computer system 102 may obtain and anonymize health care event information items associated with events associated with individuals, respectively, to generate anonymized versions of the health care event information items (or the anonymized health care event information items). With regard to an anonymized heath care event information item associated with a given individual, the anonymized health care event information item may refer to (but not specifically identify) the individual and/or refer to (but not specifically identify) the event. Computer system 102 may determine an authorized receipt of the anonymized health care event information item and generate a communication to the authorized recipient via a social media platform address associated with the authorized recipient. The generated communication may, for example, include the anonymized health care event information item, a URL to a specific portion of a website that pertains to the health care event information item (associated with the individual), or other information. Responsive to generating the communication, computer system 102 may receive, at the website, a request from the authorized recipient for access to the health care event information item. Computer system 102 may determine whether the request is authorized and, responsive to a determination that the request is authorized, system 102 may provide access to a non-anonymized version of the health care event information item.

In an implementation, information component 108 may be programmed to obtain a health care event information item associated with an event pertaining to an individual. Obtaining a health care event information item may include receiving, requesting, and/or otherwise obtaining the health care event information item. The health care event information may be obtained from one or more health care providers. The health care providers, for example, may include one or more doctors, practitioners, counselors, nurses, staff, medical and/or dental practices, hospitals, pharmacies, elderly and/or nursing home facilities, mental and/or physiatrist facilities, rehabilitation facilities, or other health providers (or their associated computer systems). The individual may include one or more of a patient, a subject of a clinical trial, a long-term care recipient, a nursing home resident, a resident of a psychiatric facility, a rehabilitation participant, and/or other individual. The health care event information item may include health care information related to a health care event pertaining to an individual. The health care event may include an event related to care and/or treatment of the individual (or other health care event). As an example, an event related to care and/or treatment of an individual may include a health incident, the passing of a period of time, an inquiry and/or request, a provider's news event and/or update, and/or other health care event related to care and/or treatment of the individual.

By way of non-limiting example, a health care event may include a provider's news event such as a lapse in a specific treatment and/or activity due to staffing issues. By way of another non-limiting example, a health care event may include the passage of a day (e.g., or other time period) with respect to a nursing home resident such that the health care information item related to the event includes a daily activity report (or other time period report) for the resident. By way of another non-limiting example, a health care event may include a prescription refill time and/or date.

Upon receipt of a health care event information item (associated with an event pertaining to an individual), anonymization component 110 may be programmed to anonymize the health care event information item to generate an anonymized health care event information item. Anonymizing a health care event information item may include one or more of generalizing, perturbing, removing personally identifiable aspects, encrypting, and/or other anonymization techniques to exclude protected health care information.

As an example, the anonymized health care event information item may refer to but not specifically identify the individual. For example, referring to (but not specifically identifying) the individual may include one or more of using a code associated with the individual, a relationship identifier, and/or other non-personal identifiers. As another example, the anonymized health care event information item may refer to but not specifically identify the event. By way of illustration, the anonymized health care event information item may refer to but not specifically identify the event by using one or more of a general notice that more information is available, a reference numeral, a code word and/or phrase, and/or other methods of referring to but not specifically identifying the event. In one use case, the anonymized health care event information item may indicate that "a family member needs to refill their prescription." In another use case, the anonymized health care event information item may include a notice that "a daily activity report is available" with or without referring to the individual.

With respect to an anonymized health care event information item (pertaining to an individual), communication component 112 may be programmed to determine an authorized recipient. An authorized recipient of the anonymized health care event information item may include the individual, someone that the individual (or other entity) pre-authorized to receive the individual's health care information, a health care surrogate, a holder of a power of attorney, a family and/or friend of the individual, or other authorized recipient. Communication component 112 may use information from various sources, such as one or more of electronic storage 124 (e.g., internal databases), external resources 122 (e.g., external databases and/or systems), the individual, user input, and/or other sources of information that may indicate one or more authorized recipients. By way of example, the daughter of a nursing home resident may be pre-authorized by the nursing home resident and/or hold a medical power of attorney, making her an authorized recipient.

Communication component 112 may be programmed to generate a communication to an authorized recipient of an anonymized health care event information item (pertaining to an individual). The communication may include one or more of a post, a message, text content, photo content, video content, audio content, and/or other types of communication and/or content. In some implementations, the generated communication may include the anonymized health care event information item, a URL to a specific portion of a website that pertains to the health care event information item, or other items.

In an implementation, communication component 112 may generate a communication (related to health care information of an individual) via a social media platform address associated with an authorized recipient. A social media platform address associated with the authorized recipient may include an address to a social media page of the authorized recipient, an account identifier that identifies the authorized recipient on the social media platform (e.g., username used by the authorized recipient for the social media platform), and/or other social media platform address (or portion thereof). In some implementations, the communication may be made accessible via the social media platform to one or more non-administrative users (of the social media platform) besides the individual and the authorized recipient. For example, a communication posted to an authorized recipient's Facebook wall may be accessible to the authorized user's "friends."

As an example, the communication may include an anonymized health care event information item (pertaining to the individual) and a URL to a specific portion of a website. In one use case, for instance, the communication may include "A family member is due for a refill of #1234. Refill by clicking on the following link: [Refill Link]." In the preceding use case, #1234 may include an anonymized hash value printed on the Rx label and linked internally to the actual patient prescription; and/or #1234 may include the trailing digits of the prescription number as it is printed on the Rx label. As such, both patient and prescription information may be anonymized. In another use case, the communication may include "A report is now available at https://www.info.com" and/or "A report for your family member is now available at https://www.info.com." The specific portion of the website may pertain to the health care event information item associated with the individual. As such, the specific portion of the website may include one or more of the health care event information item, personal health care information, provider information, available actions (e.g., requesting filling and/or refilling of a prescription, scheduling an appointment with a provider, etc.), and/or other aspects pertaining to the health care event information item.

In some implementations, a URL (and/or the specific portion of the website to which the URL refers) provided as part of a communication (related to health care information of an individual) may enable an authorized recipient to initiate one or more actions related to the health care event information item. The actions may include, for example, scheduling an appointment with a health care provider, requesting more information associated with the event pertaining to the individual, requesting to a fill a prescription, requesting a referral, and/or other actions related to the health care event information item. In some implementations, the communication may include two or more URLs. As an example, one URL may be a link to the specific portion of the website and the other URL may be a link to initiate one or more actions related to the health care event information item.

Authorization component 114 may be programmed to receive a request for access to a health care event information item pertaining to an individual. As an example, upon receipt of a communication that includes a URL to a specific portion of a website that pertains to the health care event information item, an authorized recipient may activate the URL to cause a submission of the request to the website for access to the health care event information item. Upon receipt of the request, the website may forward the request to authorization component 114 to determine whether the request should be authorized. As a further example, authorization component 114 may cause the website to prompt the authorized recipient for a username and/or password, which may be utilized to assess whether authorization for access to the health care event information item is to be granted.

Authorization component 114 may be programmed to provide access to a non-anonymized version of a health care event information item pertaining to an individual. Access to the non-anonymized version of the health care event information item may be provided to a requesting user (e.g., an authorized receipt of the anonymized version of the health care event information item) responsive to a determination that the user's request for access should be authorized. By way of illustration, responsive to the user inputting the correct user name and ID associated with the authorized recipient, the website may display the non-anonymized version of the health care event information item, such as a full daily progress report pertaining to the individual, prescription refills available for the individual and related details, or other information.

Facilitation of Health Care Services Via Social Media

In an implementation, computer system 102 may enable users to request health care services (e.g., requests for more information regarding an event pertaining to an individual, requests for scheduling an appointment with a health care provider, requests for filling and/or refilling a prescription, etc.) via social media. In some implementations, computer system 102 may receive a social media communication of a user from a social media platform. Computer system 102 may process the social media communication to determine a health care service (e.g., requested by the user on behalf of the user, on behalf of an individual related to the user, etc.) and generate a user request for the health care service (e.g., based on information regarding a health care service provider that is able to provide the health care service, patient information of the individual (or the user) on whose behalf the health care service is requested, or other information). The user request may then be provided to the health care service provider.

In an implementation, communication component 112 may be programmed to receive a social media communication of a user from a social media platform. A social media platform, for example, may include a social media platform such as Facebook, Twitter, Instagram, MySpace, Pinterest, LinkedIn, and/or other social media platform. In some implementations, content in and/or from a social media platform may be public and/or partially available to the public. The social media communication may be received via a social media platform address associated with computer system 102 (or an entity associated therewith).

As an example, the social media communication may include a tag provided by a user (e.g., "#System 1234 " where System 1234 is a username on the social media platform) to specify the user's intent that computer system 102 (or an entity associated therewith) receive the social media communication. Thus, based on the tag, the social media platform may make the social media communication accessible via the social media address associated with computer system 102 (or an entity associated therewith). In one use case, for instance, all social media communication that includes "#System1234 " may be made accessible via the social media address associated with the system 102 (or an entity associated therewith) (e.g., the associated entity's social media page on the social media platform), and communication component 112 may be programmed to obtain the social media communications that are made accessible via the social media address (e.g., on a periodic basis, based on detection of an "unread" social media communication, etc.).

In some implementations, a social media communication may indicate a health care service. A health care service may include a service provided by and/or related to a health care provider. A service provided by and/or related to a health care provider may include, for example, one or more of communicating health care information, providing a referral, scheduling a health care appointment, communicating prescription alternatives, filling and/or refilling a prescription, and/or other health care service. The social media communication may indicate a health care service for a user (that provided the social media communication) and/or for an individual related to the user. The user may be authorized to communicate and/or indicate health care services on behalf of the individual or otherwise related to the individual (e.g., family relationship, other social relationship, etc.). In some implementations, a hashtag (or other tag) may indicate the health care service. In one use case, a user may provide the hashtag "#SystemRefill" in a social media communication to computer system 102 to specify a request by the user to fill a prescription (e.g., on behalf of an individual for which the user is authorized to request prescription refills).

In some implementations, communication component 112 may be programmed to generate a reminder communication for a user via a social media platform address associated with the user. The reminder communication may include an anonymized reminder related to one or more actions that are to be taken by the user or an individual related to the user. For example, communication component 112 may generate a reminder to the user indicating that a prescription refill is available, causing the reminder to be provided for presentation to the user via the social media platform. In response, the user may reply with (or otherwise provide) the communication "I want to request 1234 #SystemRefill" via the social media platform, which may be received by communication component 112.

Upon receipt of a social media communication, social media processing component 116 may be programmed to process the social media communication to determine whether the social media communication indicates a health care service. As an example, if the social media communication includes "I need to request 1234, " the word "request" together with the code "1234 " (corresponding to a particular prescription, the particular individual to whom the prescription is provided, etc.) may be determined by social media processing component 116 as a request for a prescription refill on behalf of the particular individual (e.g., the user or an related individual).

As another example, if the social media communication includes "I would like to make a schedule request," social media processing component 116 may interpret the words "I," "like," and "schedule request" as a request to schedule a doctor appointment for the user or their dependents. Social media processing component 116 may process the user's profile information to determine the identity of the user and/or other information for scheduling the appointment. In some implementations, the user's profile information may indicate whether the user is authorized to request health care services on behalf of a family member, dependent, designated care recipient, and/or other subject.

Service information component 118 may be programmed to obtain information associated with a health care service (e.g., a requested health care service). The information may include a preferred health care service provider (e.g., preferred by the individual who will receive the health care service, preferred by the user, preferred by a health plan of the individual who will receive the health care service, etc.). The information associated with the health care service may be obtained from one or more internal and/or external sources. For example, information associated with the health care service may be obtained from one or more of electronic storage 124, client computing platforms 104, and/or external resources 122. Electronic storage 124 may include one or more databases and/or other stored information associated with one or more users of system 100. External resources 122 may include one or more of an external database, a health care provider system, a health care provider database, health care provider profiles, and/or other external resources. In some implementations, if a preferred provider is known, information (or additional information) associated with the health care service may be obtained from the preferred provider's system.

In some implementations, information associated with a health care service may include user information, patient information, health care service information, health care service provider information, and/or other information. User information may include user-identifying information, past user actions, preferred health care service providers, user health care information, and/or other information associated with the user. For example, user information may include a preferred health care service provider such as a preferred pharmacy for refilling a prescription and/or a preferred primary care physician (e.g., with whom to schedule appointments). Patient information may be similar to user information but pertain to an individual other than the user (e.g., if the user and the individual are not the same).

Health care service information may include prescription information, service information, progress and/or status information, and/or other information. In some implementations, health care service information, for example, may include prescription information such as a quantity, dosage, brand, prescription number, and/or other prescription information. Health care service provider information may include contact information, request format information, request method information, and/or other information. For example health care service provider information may include an address, a phone number, a health care service request format, a web address, and/or other information.

Request component 120 may be programmed to generate a user request for a health care service. As an example, based on a social media communication indicating a health care service, request component 120 may generate a user request for the indicated health care service. The user request may be properly formatted and/or structured to provide to the health care service provider. For example, the social media communication may include a natural language request for a health care service that the health care service provider may not be able to understand. In one use case, for instance, the social media communication may include "I want to request 1234." Upon determining that the social media communication indicates a request related to a refill of a certain prescription for a particular individual (e.g., based on the code "1234 " corresponding to the prescription, the individual, etc.) and selecting a service provider to fulfill the refill request, request component 120 may obtain formatting instructions specific to the selected service provider (e.g., a predefined set of formatting instructions specified by the selected service provider). Request component 120 may then generate the refill request in accordance with the obtained formatting instructions.

In some implementations, the user request for the health care service may be generated based on information associated with the health care service. User requests may have various requirements (e.g., required and/or optional formatting, required and/or optional parameters, etc.) based on the requested health care service, the health care service provider that is selected to provide the requested health care service, and/or other criteria. In some implementations, the user request may be generated in accordance with a required format of the health care service provider that is selected to provide the requested health care service.

In an implementation, different health care service providers may require different formats and/or parameters for service requests. For example, a user request for a prescription refill by one provider may be generated to have a first set of parameters in accordance with a first set of formatting instructions, while a user request for the same prescription refill by another provider may be generated to have a second set of parameters with a second set of formatting instructions. In another implementation, the method of sending user requests to the health care service providers may be different. As an example, one provider may require refill requests to be submitted electronically (e.g., via its website), while another provider only accepts refill requests via physical mail.

Communication component 112 may be programmed to provide a user request for a health care service to a health care service provider. The user request may be provided via one or more of a website, an email, an automated telephone call, mailing a paper request, a fax, and/or other methods of providing and/or communicating the user request to the preferred health care service provider.

In some implementations, communication component 112 may be programmed to generate a response (or response communication) to a user's social media communication via a social media platform address associated with the user. As an example, if the user's social media communication is related to a user request for a health care service, the response communication may include a response to or an update for the user request. The response communication may be generated based on a response and/or communication from the health care service provider. The update and/or response may notify the user of a status of the user request.

For example, responsive to communication component 112 providing a user request for a prescription refill to the preferred pharmacy, communication component 112 may receive a response from the pharmacy that the prescription refill has been filled, and generate a response communication for presentation to the user via a social media platform. The response communication may be anonymized (e.g., generalized, perturbed, etc.). For example, the response communication may include "Your 1234 request has been filled." In some implementations, the response communication may be based on information from one or more outside sources such as a mail and/or delivery service. For example, the response communication may include "Your 1234 request is on its way."

Returning to FIG. 1, computer system 102 (e.g., one or more servers), client computing platforms 104, external resources 122, and/or other components may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which computer system 102, client computing platforms 104, external resources 122, and/or other components may be operatively linked via some other communication media.

A given client computing platform 104 may include one or more processors programmed to execute computer program components. The computer program components may be programmed to enable an expert or user associated with client computing platform 104 to interface with system 100 and/or external resources 122, and/or provide other functionality attributed herein to client computing platforms 104. By way of non-limiting example, client computing platform 104 may include one or more of a desktop computer, a laptop computer, a handheld computer, a netbook, a smartphone, a gaming console, and/or other computing platforms.

External resources 122 may include sources of information, hosts and/or databases outside of system 100, external entities participating with system 100, and/or other resources. In some implementations, some or all of the functionality attributed herein to external resources 122 may be provided by resources included in system 100.

In some implementations, computer system 102 may include electronic storage 124, one or more processors 106, and/or other components. Computer system 102 may include communication lines, or ports to enable the exchange of information with a network and/or other computing platforms. Illustration of computer system 102 in FIG. 1 is not intended to be limiting. Computer system 102 may include a plurality of hardware, software, and/or firmware components operating together to provide the functionality attributed herein to computer system 102. For example, computer system 102 may be implemented by a cloud of computing platforms operating together as computer system 102.

Electronic storage 124 may comprise non-transitory storage media that electronically stores information. The electronic storage media of electronic storage 124 may include one or both of system storage that is provided integrally (i.e., substantially non-removable) with computer system 102 and/or removable storage that is removably connectable to computer system 102 via, for example, a port (e.g., a USB port, a firewire port, etc.) or a drive (e.g., a disk drive, etc.). Electronic storage 124 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 124 may include one or more virtual storage resources (e.g., cloud storage, a virtual private network, and/or other virtual storage resources). Electronic storage 124 may store software algorithms, information determined by processor(s) 106, information received from computer system 102, information received from client computing platforms 104, and/or other information that enables computer system 102 to function as described herein.

Processor(s) 106 is programmed to provide information processing capabilities in computer system 102. As such, processor(s) 106 may include one or more of a digital processor, an analog processor, a digital circuit designed to process information, an analog circuit designed to process information, a state machine, and/or other mechanisms for electronically processing information. Although processor(s) 106 is shown in FIG. 1 as a single entity, this is for illustrative purposes only. In some implementations, processor(s) 106 may include a plurality of processing units. These processing units may be physically located within the same device, or processor(s) 106 may represent processing functionality of a plurality of devices operating in coordination. Processor(s) 106 may be programmed to execute components 108, 110, 112, 114, 116, 118, 120, and/or other components. Processor(s) 106 may be programmed to execute components 108, 110, 112, 114, 116, 118, 120, and/or other components by software; hardware; firmware; some combination of software, hardware, and/or firmware; and/or other mechanisms for configuring processing capabilities on processor(s) 106. As noted, in certain implementations, a client computing platform 104 may include one or more computer program components that are the same as or similar to the computer program components of computer system 102. Client computing platform 104 may include one or more processors that are the same or similar to processor(s) 106 of computer system 102 to execute the computer program components of client computing platform 104.

Figure 2:
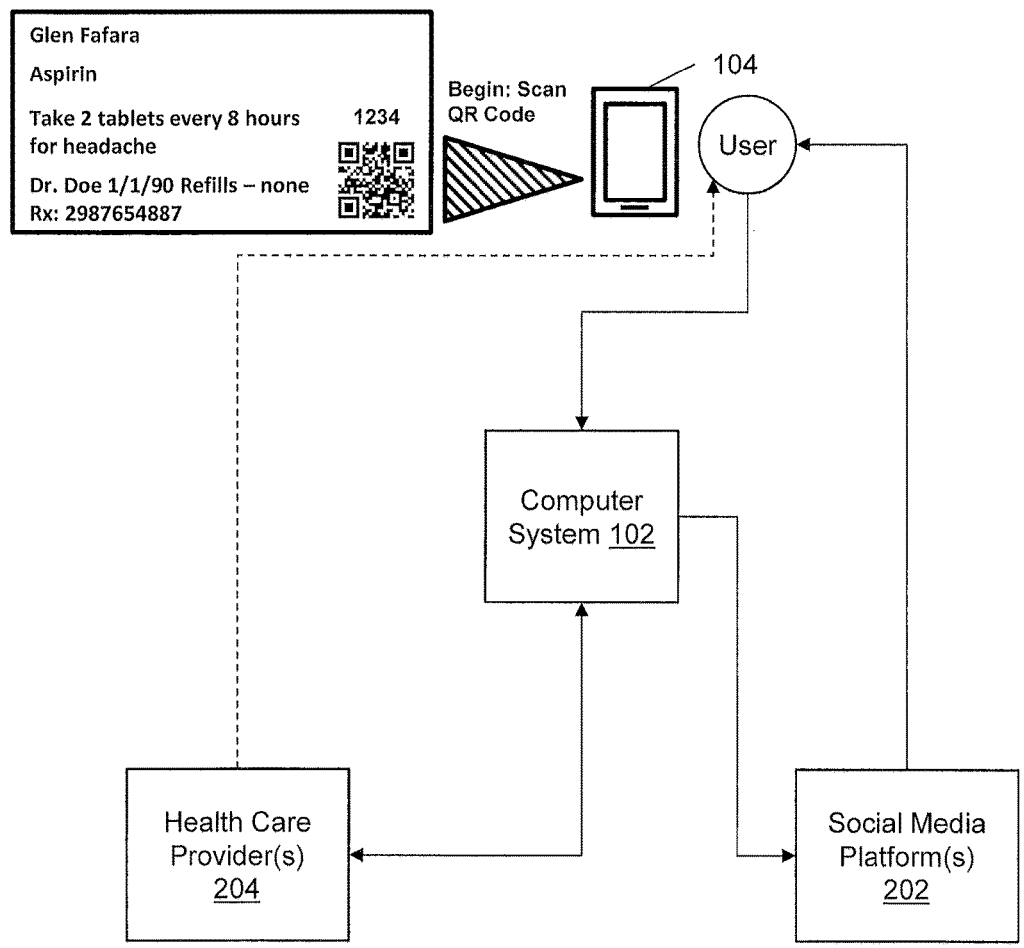
FIGS. 2-4 illustrate use cases of communicating health care information and/or facilitating health care services via a hybrid architecture, in accordance with various implementations.
Figure 3:
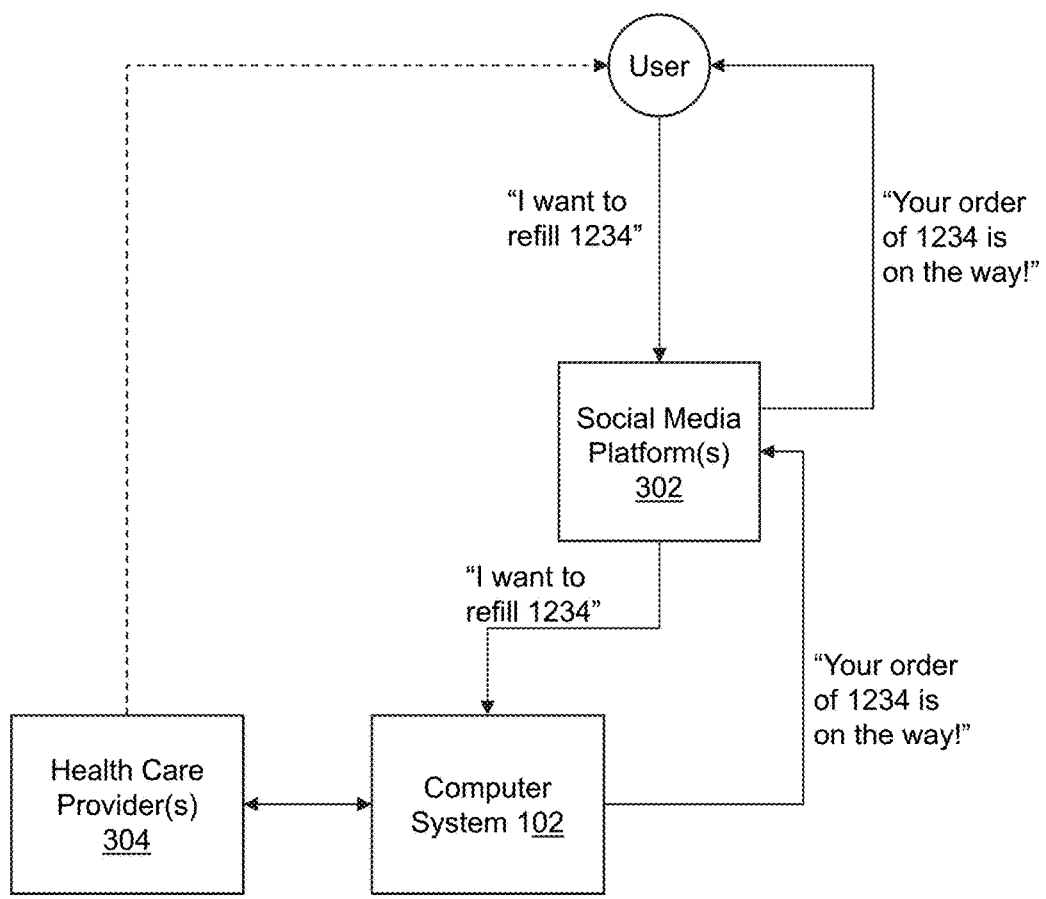
Figure 4:
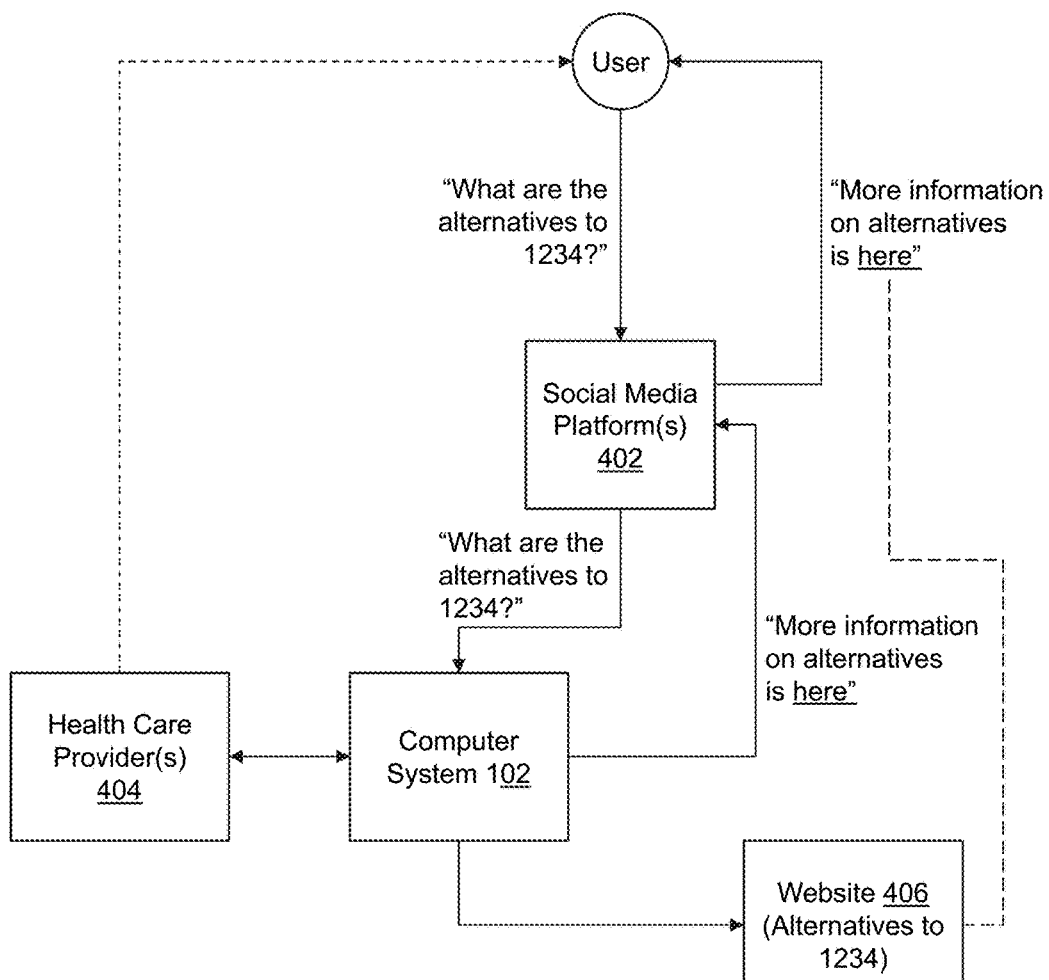

FIGS. 2-4 illustrate use cases of communicating health care information and/or facilitating health care services via a hybrid architecture, in accordance with various implementations. In an implementation, with respect to FIG. 2, a user may utilize client computing device 104 (or a client application thereof) to scan a QR code that corresponds to a specific encoded service request, and/or portion of a website that pertains to one or more aspects of an individual's care and/or treatment. The scanning of the QR code may, for instance, cause client computing device 104 to identify a URL to the specific portion of the website, a unique identifier to request a particular health care service, pass anonymized service request parameters (e.g., a prescription hash value for a refill), and/or other information. Client computing device 104 may load the specific portion of the website (e.g., by accessing computer system 102 using the URL) and/or provide the identified information to computer system 102 for further processing.

As an example, if the QR code corresponds to providing the user with additional information about a certain prescription, the specific portion of the website may enable the user to view the additional information regarding the prescription, and computer system 102 may provide the specific portion of the website for presentation to the user. The specific portion of the website may further enable the user to initiate one or more other actions related to the prescription (e.g., request a refill of the prescription) or actions related to the care and/or treatment of the individual.

As another example, if the QR code corresponds to a request for refilling the prescription, the URL to the specific portion of the website may include the unique anonymized identifier for requesting the refill. As such, upon loading the URL, computer system 102 may automatically generate a user request for the refilling of the prescription, and provide the user request to health care provider 204. As a further example, health care provider 204 may notify computer system 102 regarding one or more events upon their occurrence, such as a confirmation of receipt of the request, a confirmation that the refill is ready for pick up and/or has been shipped, a notification of the location at which the refill can be picked up or to which it has been shipped, etc. In response to receiving a notification from health care provider 204, computer system 102 may anonymize the notification and generate, via a social media address associated with the user, a social media communication including the anonymized notification. As a result, for instance, social media platform 202 may make the anonymized notification accessible to the user on the user's social media page on social media platform 202.

In an implementation, with respect to FIG. 2, a user may utilize client computing device 104 (or a client application thereof) to scan the QR code to identify a message that is to be posted on the user's social media platform (e.g., social media platform 202) as a social media communication of the user. As an example, upon scanning the QR code, client computing device 104 may identify the message as "#System 102 Request 1234," and post the message on the user's social media page on social media platform 202. If, for example, System 102 is a username used by an entity associated with computer system 102 on social media platform 202, the message may be posted on the associated entity's social media page. The posting of the message may prompt computer system 102 to interpret the message and generate an appropriate user request for refilling a certain prescription (e.g., corresponding to the code 1234) for a particular individual (e.g., corresponding to the code 1234) that is to be provided to health care provider 204.

In an implementation, with respect to FIG. 4, a user may post social media communications on social media platform 402 to initiate requests for informational health care services (e.g., on behalf of an individual related to the user). As an example, the user may post the social media communication "What are the alternatives to 1234 ?" on a social media page of computer system 102 (or an entity associated therewith) on social media platform 402. The posting of the message may prompt computer system 102 to interpret the message and generate, via a social media address associated with the user, a social media communication in accordance with the interpretation of the message. If, for example, the message is interpreted as a request for more information regarding alternative prescriptions to the prescription corresponding to code 1234, computer system 102 may generate a message that includes the anonymized message "More information on alternatives is here," where "here" is a hyperlink to website 406. Website 406 may, for example, include information regarding alternative prescriptions to the prescription corresponding to code 1234.

As a further example, website 406 may be provided by health care provider 404. Upon interpretation of the message, computer system 102 may generate and/or provide a request for more information regarding alternative prescriptions to the prescription corresponding to the code 1234 to health care provider 404. In response, health care provider 404 may provide a URL for a specific portion of website 406 to computer system 102 that includes information regarding the alternative prescriptions. Computer system 102 may then generate the social media communication "More information on alternatives is here" where "here" is a hyperlink using the URL, and the social media communication is thereafter made accessible to the user such that the user may utilize the hyperlink "here" to access the specific portion of website 406 that includes information regarding the alternative prescriptions. The provider may secure these web pages using one or more of OAuth, two part user-id/password credentials, and/or other security measures.

In an implementation, with respect to FIG. 3, a user may post social media communications on social media platform 302 to initiate requests for health care services (e.g., on behalf of an individual related to the user). As an example, the user may post the social media communication "I want to request 1234 " on a social media page of computer system 102 (or an entity associated therewith) on social media platform 302. The posting of the message may prompt computer system 102 to interpret the message and generate an appropriate user request for refilling a certain prescription (e.g., corresponding to the code 1234) for a particular individual (e.g., corresponding to the code 1234) that is to be provided to health care provider 304. As a further example, health care provider 304 may notify computer system 102 regarding one or more events upon their occurrence. As indicated in FIG. 3, health care provider 304 may notify computer system 102 when the requested refill order has been shipped. In response to receiving the notification, computer system 102 may anonymize the notification and generate, via a social media address associated with the user, a social media communication including the anonymized notification (e.g., "Your order of 1234 is on the way!"). As a result, for instance, social media platform 302 may make the anonymized notification accessible to the user on the user's social media page on social media platform 302.

Figure 5:
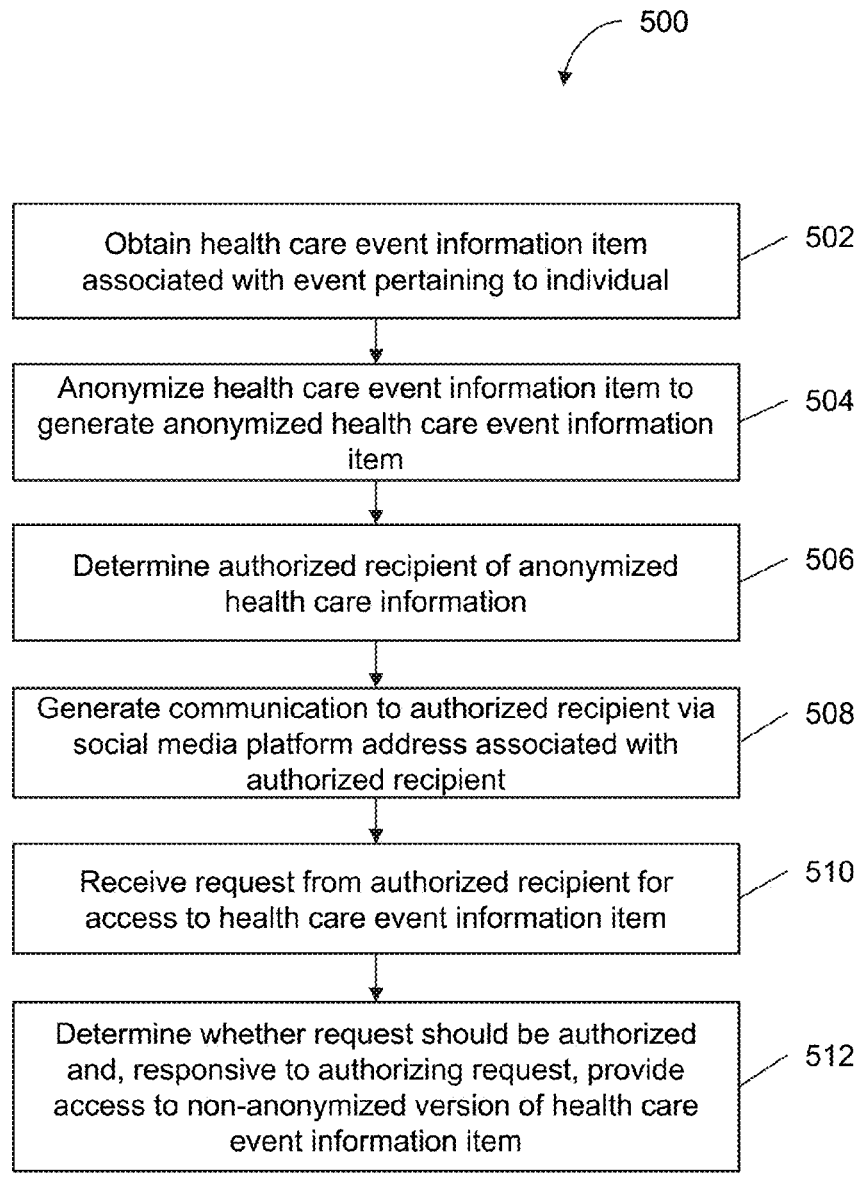
FIG. 5 illustrates a method for communicating health care information and/or facilitating health care services via a hybrid architecture, in accordance with an implementation.

FIG. 5 illustrates a method for communicating health care information via a hybrid architecture including a social media component and a website. The operations of method 500 presented below are intended to be illustrative. In some implementations, method 500 may be accomplished with one or more additional operations not described, and/or without one or more of the operations discussed. Additionally, the order in which the operations of method 500 are illustrated in FIG. 5 and described below is not intended to be limiting.

In some implementations, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices programmed through hardware, firmware, and/or software to be specifically designed for execution of one or more of the operations of method 500.

At operation 502, a health care event information item associated with an event pertaining to an individual may be obtained. For example, a health care event information item associated with an event pertaining to an individual may include a daily progress report for a nursing home patient. Operation 502 may be performed by an information component that is the same as or similar to information component 108, in accordance with one or more implementations.

At operation 504, the health care event information item may be anonymized to generate an anonymized health care event information item. The anonymized health care event information item may refer to (but not specifically identify) the individual and refer to (but not specifically identify) the event. For example, the anonymized health care event information item may indicate that a report for a close family member is available. Operation 504 may be performed by an anonymization component that is the same as or similar to anonymization component 110, in accordance with one or more implementations.

At operation 506, an authorized recipient of the anonymized health care event information item may be determined. For example, a social media user authorized (e.g., in a HIPAA compliant manner) to receive anonymized health care event information, such as a daughter of the nursing home patient holding a medical power of attorney, may be determined. Operation 506 may be performed by a communication component that is the same as or similar to communication component 112, in accordance with one or more implementations.

At operation 508, a communication to the authorized recipient may be generated via a social media platform address associated with the authorized recipient. The communication may include the anonymized health care event information item and a URL. The URL may be to a specific portion of the website that pertains to the health care event information item associated with the individual. The specific portion of the website may be secured by a user-id and password. For example, the communication may be posted to the daughter's Facebook page. By way of this example, the communication may indicate that a report for a charge of the recipient is available and include a link to view the full daily progress report. Operation 508 may be performed by a communication component that is the same as or similar to communication component 112, in accordance with one or more implementations.

At operation 510, a request from the authorized recipient for access to the health care event information item associated with the URL may be received. The request may be received at a website. For example, if the authorized user, such as the daughter of the nursing home patient, clicks on the URL, she may request authorization from the website to view the health care event information item such as the daily progress report. Operation 510 may be performed by an authorization component that is the same as or similar to authorization component 114, in accordance with one or more implementations.

At operation 512, a determination of whether the request should be authorized may be effectuated. In response to a determination that the request should be authorized, access to a non-anonymized version of the health care event information item may be provided. By way of a non-limiting example, the system may determine if the request should by authorized by requiring a password and in response to the correct password being entered, access to the non-anonymized version of the health care event information item such as a progress report may be authorized. Operation 512 may be performed by an authorization component that is the same as or similar to authorization component 114, in accordance with one or more implementations.

Figure 6:
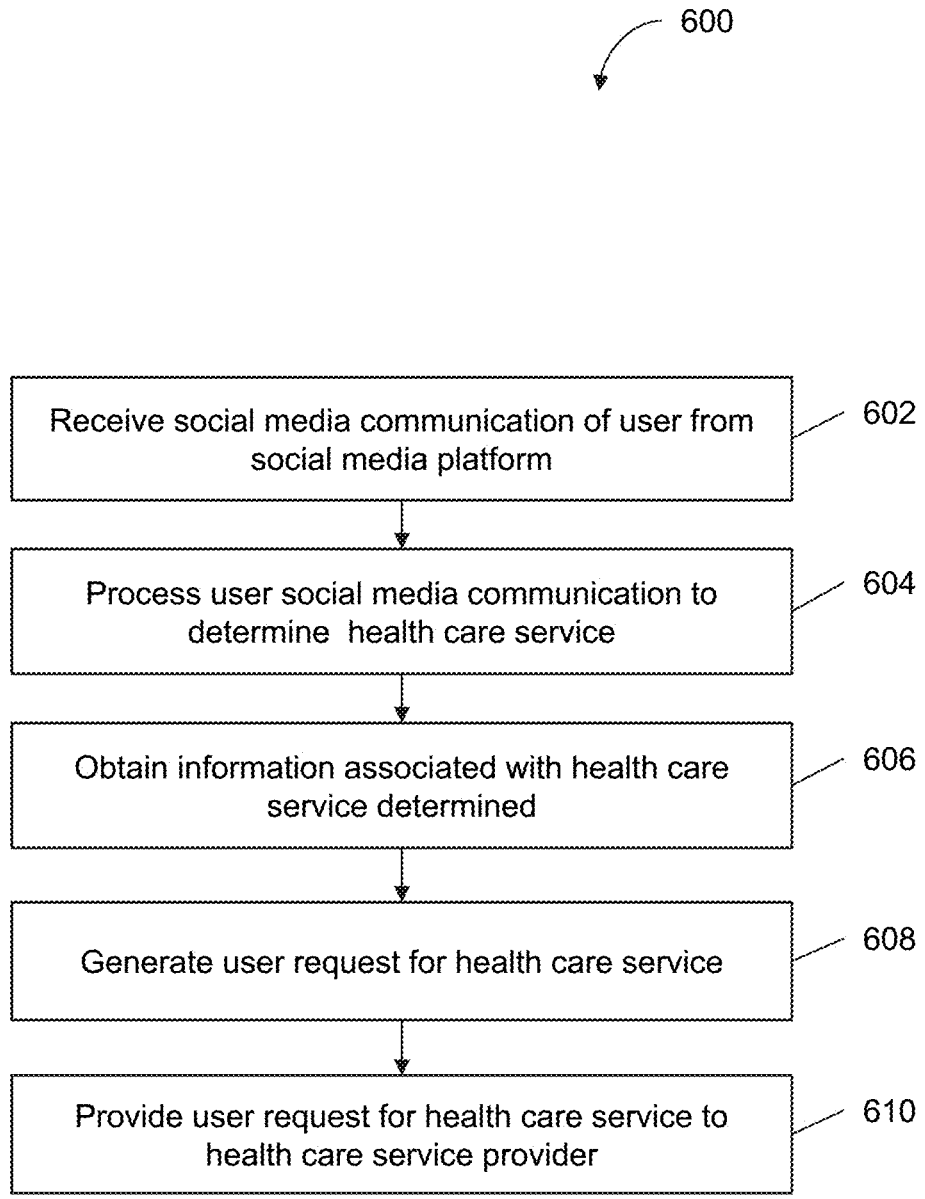
FIG. 6 illustrates a method for communicating health care information and/or facilitating health care services via a hybrid architecture, in accordance with another implementation.

FIG. 6 illustrates a method for facilitating health care services via a hybrid architecture including a social media component and a website. The operations of method 600 presented below are intended to be illustrative. In some implementations, method 600 may be accomplished with one or more additional operations not described, and/or without one or more of the operations discussed. Additionally, the order in which the operations of method 600 are illustrated in FIG. 6 and described below is not intended to be limiting.

In some implementations, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices programmed through hardware, firmware, and/or software to be specifically designed for execution of one or more of the operations of method 600.

At operation 602, a social media communication of a user may be received from a social media platform. The social media communication may indicate a health care service. For example, a user tweet of "I want to request 1234 #SMSRX" may be received and may indicate a prescription refill. Operation 602 may be performed by a communication component that is the same as or similar to communication component 112, in accordance with one or more implementations.

At operation 604, the user social media communication may be processed to determine a health care service. For example, the user tweet of "I want to request 1234 #SMSRX" may be processed to determine the health care service the user indicated is a prescription refill of a medication. Operation 604 may be performed by a social media processing component that is the same as or similar to social media processing component 116, in accordance with one or more implementations.

At operation 606, information associated with the health care service may be obtained. The information may include a health care service provider. The health care service provider may be the health care service provider pre-selected by the user. For example, the information associated with the health care service may include which pharmacy a user typically uses and/or whether a refill is available for a medication. Operation 606 may be performed by a service information component that is the same as or similar to service information component 118, in accordance with one or more implementations.

At operation 608, a user request for the health care service may be generated. For example, a refill request for refilling of a prescription (that is to be provided by a particular health care service provider) may be generated. Operation 608 may be performed by a request component that is the same as or similar to request component 120, in accordance with one or more implementations.

At operation 610, the user request for the health care service may be provided to the health care service provider. For example, a refill request generated may be provided to the user's preferred pharmacy indicated by the information associated with the health care service. Operation 610 may be performed by a communication component that is the same as or similar to communication component 112, in accordance with one or more implementations.

Although the system(s) and/or method(s) of this disclosure have been described in detail for the purpose of illustration based on what are currently considered to be the most practical and preferred implementations, it is to be understood that such detail is solely for that purpose and that the disclosure is not limited to the disclosed implementations, but, on the contrary, is intended to cover modifications and equivalent arrangements that are within the spirit and scope of the appended claims. For example, it is to be understood that the present disclosure contemplates that, to the extent possible, one or more features of any implementation can be combined with one or more features of any other implementation.

What is claimed is:

1. A method for communicating health care information via a hybrid architecture including a social media platform and a website external to the social media platform, comprising:

obtaining, by a computer system, a first health care event information item associated with an event pertaining to a first individual;

generating, by the computer system, a first hash value that represents at least part of the first health care event information item;

generating, by the computer system, an anonymized version of the first health care event information item that comprises the first hash value such that the anonymized version of the first health care event information item refers to but does not specifically identify the first individual and refers to but does not specifically identify the event, wherein the anonymized version of the first health care event information item comprises the first hash value in lieu of the at least part of the first health care event information that the first hash value represents;

determining, by the computer system, an authorized recipient of the anonymized version of the first health care event information item;

generating, by the computer system, a first communication at the social media platform to the authorized recipient using a social media platform address associated with the authorized recipient such that the first communication is accessible to the authorized recipient and other non-administrative users of the social media platform that are permitted to access communications directed to the authorized recipient, wherein the first communication comprises the anonymized version of the first health care event information item and a URL to a specific portion of the website that pertains to the first health care event information item associated with the first individual, wherein the URL enables the authorized recipient to initiate a request to fill and/or refill a prescription, and the URL comprises the first hash value as a parameter related to the request to fill and/or refill the prescription, and wherein, responsive to the generation of the first communication at the social media platform, the first hash value is accessible to the authorized recipient and the other non-administrative users of the social media platform;

receiving, at the website external to the social media platform, via the first communication, a request from the authorized recipient for access to the first health care event information item associated with the URL, wherein the request received at the website is based on the first hash value in the URL; and determining, by the computer system, if the request should be authorized, and, in response to a determination that the request should be authorized, providing access to a non-anonymized version of the first health care event information item.

2. The method of claim 1, further comprising:
obtaining, by the computer system, a second health care event information item associated with a second event pertaining to a second individual;
generating, by the computer system, an anonymized version of the second health care event information item that refers to but does not specifically identify the second individual and refers to but does not specifically identify the second event;
determining, by the computer system, an authorized recipient of the anonymized version of the second health care event information item; and
generating, by the computer system, a second communication at the social media platform to the authorized recipient using a social media platform address associated with the authorized recipient, wherein the second communication comprises the anonymized version of the second health care event information item and a second URL to a specific portion of the website that pertains to the second health care event information item associated with the second individual.

3. The method of claim 1, wherein the specific portion of the website enables the authorized recipient to initiate one or more actions related to the first health care event information item, and wherein the one or more actions include one or more of scheduling of an appointment with a health care provider, requesting more information associated with the event pertaining to the first individual, or requesting to a fill and/or refill a prescription.

4. The method of claim 1, further comprising:
associating, by the computer system, the first hash value with the at least part of the first health care event information item,
wherein providing access to the non-anonymized version of the first health care event information item comprises obtaining, based on the first hash value, the non-anonymized version of the first health care event information item.

5. The method of claim 1, wherein the authorized recipient includes the first individual.

6. The method of claim 1, wherein the authorized recipient includes a user other than the first individual that the first individual pre-authorized to receive the anonymized version of the first health care event information item and/or the non-anonymized version of the first health care event information item.

7. The method of claim 1, wherein generating the first hash value comprises hashing the at least part of the first health care event information item to generate the first hash value.

8. The method of claim 1, wherein obtaining the first health care event information item includes obtaining the first health care event information item from a health care provider.

9. The method of claim 1, wherein the first health care event information item includes information associated with one or more of an available prescription refill, a status or activity update, or a progress report.

10. A system for communicating health care information via a hybrid architecture including a social media platform and a website external to the social media platform, the system comprising:
a computer system comprising one or more physical processors programmed with computer program instructions which, when executed, cause the computer system to:
obtain a first health care event information item associated with an event pertaining to a first individual;
generate a first hash value that represents at least part of the first health care event information item;
generate an anonymized version of the first health care event information item that comprises the first hash value such that the anonymized version of the first health care event information item refers to but does not specifically identify the first individual and refers to but does not specifically identify the event, wherein the anonymized version of the first health care event information item comprises the first hash value in lieu of the at least part of the first health care event information that the first hash value represents;
determine an authorized recipient of the anonymized version of the first health care information item;
generate a first communication at the social media platform to the authorized recipient using a social media platform address associated with the authorized recipient such that the first communication is accessible to the authorized recipient and other non-administrative users of the social media platform that are permitted to access communications directed to the authorized recipient,
wherein the first communication comprises the anonymized version of the first health care event information item and a URL to a specific portion of the website that pertains to the first health care event information item associated with the first individual, wherein the URL enables the authorized recipient to initiate a request to fill and/or refill a prescription, and the URL comprises the
first hash value as a parameter related to the request to fill and/or refill the
prescription, and wherein, responsive to the generation of the first communication at the social media platform, the first hash value is accessible to the authorized recipient and the other non-administrative users of the social media platform;
receive, at the website external to the social media platform, via the first communication, a request from the authorized recipient for access to the first health care event information item associated with the URL, wherein the request received at the website is based on the first hash value in the URL; and
determine if the request should be authorized, and in response to a determination that the request should be authorized, provide access to a non-anonymized version of the first health care event information item.

11. The system of claim 10, wherein the computer system is further caused to:
obtain a second health care event information item associated with a second event pertaining to a second individual;
generate an anonymized version of the second health care event information item that refers to but does not specifically identify the second individual and refers to but does not specifically identify the second event;
determine an authorized recipient of the anonymized version of the second health care event information item; and
generate a second communication at the social media platform to the authorized recipient using a social media platform address associated with the authorized recipient, wherein the second communication comprises the anonymized version of the second health care event information item and a second URL to a specific portion of the website that pertains to the second health care event information item associated with the second individual.

12. The system of claim 10, wherein the specific portion of the website enables the authorized recipient to initiate one or more actions related to the first health care event information item, and wherein the one or more actions include one or more of scheduling of an appointment with a health care provider, requesting more information associated with the event pertaining to the first individual, or requesting to a fill and/or refill a prescription.

13. The system of claim 10, wherein the computer system is further caused to:
    associate the first hash value with the at least part of the first health care event information item,
    wherein the computer system provides access to the non-anonymized version of the first health care event information item by obtaining, based on the first hash value, the non-anonymized version of the first health care event information item.

14. The system of claim 10, wherein the authorized recipient includes the first individual.

15. The system of claim 10, wherein the authorized recipient includes a user other than the first individual that the first individual pre-authorized to receive the anonymized version of the first health care event information item and/or the non-anonymized version of the first health care event information item.

16. The system of claim 10, wherein the computer system generates the first hash value by hashing the at least part of the first health care event information item to generate the first hash value.

17. The system of claim 10, wherein the computer system obtains the first health care event information item from a health care provider.

18. The system of claim 10, wherein the first health care event information item includes information associated with one or more of an available prescription refill, a status or activity update, or a progress report.

\* \* \* \* \*